United States Patent [19]
Yaginuma et al.

[11] Patent Number: 4,749,571
[45] Date of Patent: Jun. 7, 1988

[54] PHYSIOLOGICALLY-ACTIVE NOVEL SUBSTANCE "ALDOSTATIN" AND PRODUCTION METHOD THEREOF

[75] Inventors: Satoshi Yaginuma, Yokka; Akira Asahi; Masaki Takada, both of Shizuoka, all of Japan

[73] Assignee: Toyo Jozo Co., Ltd., Shizuoka, Japan

[21] Appl. No.: 16,327

[22] Filed: Feb. 19, 1987

[30] Foreign Application Priority Data

Mar. 4, 1986 [JP] Japan ................. 61-45327

[51] Int. Cl.$^4$ .................. A61K 35/70; C12P 1/02
[52] U.S. Cl. ...................... 424/119; 424/120; 435/171
[58] Field of Search ............... 424/119, 120; 435/171

[56] References Cited

FOREIGN PATENT DOCUMENTS

| 0036713 | 2/1981 | European Pat. Off. |
| 0045161 | 7/1981 | European Pat. Off. |
| 0047014 | 9/1981 | European Pat. Off. |
| 0095229 | 3/1983 | European Pat. Off. |
| 0148752 | 1/1985 | European Pat. Off. |
| 0161796 | 9/1985 | European Pat. Off. |
| 2001061 | 6/1978 | United Kingdom . |
| 2012274 | 12/1978 | United Kingdom . |
| 2011389 | 12/1978 | United Kingdom . |
| 2024814 | 6/1979 | United Kingdom . |
| 2037754 | 11/1979 | United Kingdom . |

OTHER PUBLICATIONS

Chemical Abstracts, Registry No. 13200-86-7 (N-formyltyrosin).

Primary Examiner—Jerome D. Goldberg
Attorney, Agent, or Firm—Oblon, Fisher, Spivak, McClelland & Maier

[57] ABSTRACT

A physiologically-active novel substance "aldostatin" having an estimated molecular formula of $C_{20}H_{20}N_2O_8$ is produced by culturing an aldostatin-producing microorganism of the Pseudeurotium, for example, the *Pseudeurotium zonatum* M4109 strain. Aldostatin inhibits the aldose reductase activity and as a consequence, avoids abnormal accumulation of sorbitol, galactitol, etc. It is therefore effective for the treatment of chronic complications such as cataract, retinopathy and neuropathy caused by diabetes renalis.

2 Claims, 6 Drawing Sheets

PHYSIOLOGICALLY-ACTIVE NOVEL SUBSTANCE "ALDOSTATIN" AND PRODUCTION METHOD THEREOF

BACKGROUND OF THE INVENTION

1. Field of the Invention

This invention relates to a physiologically-active novel substance "aldostatin", which is an aldose reductase inhibitor, and its salts as well as a production method thereof. Aldostatin, which the present invention provides, is useful for the treatment of certain chronic complications caused by diabetes renalis, such as diabetogenous cataract, retinopathy and neuropathy.

2. Description of the Prior Art

The reduction of blood sugar level has been the subject of a majority of attempts which have heretofore been made to obtain antidiabetic drugs. Under the circumstances, almost no means is however known for the prevention or reduction of chronic diabetogenous complications such as diabetogenous cataract, retinopathy and neuropathy. According to Sakamoto et al. ["Pharmacia" 19, 43, (1983)], the metabolism in the polyol system is activated by slight sthenia of an aldose reductase in a state of high blood sugar level such as diabetic, resulting in further promotion of the abnormal accumulation of sorbitol, galactitol and fructose. These sorbitol, galactitol and fructose are relatively stable in cells. Once they are formed there, their transit to the outside of the cells is scarcely observed. This disturbance to the balanced production and excretion leads to the intracellular accumulation of such sugar alcohols. This is in turn considered to cause accumulation of water in cells so that the cells can no longer maintain their normal function, resulting in a histionic problem. It has hence been considered that the abnormal intracellular accumulation of sorbitol, galactitol and fructose can be avoided and the cellular function can be maintained normal if the activities of the aldose reductase are inhibited.

Accordingly, there has been a long-standing demand for the provision of a novel aldose reductase inhibitor useful for the prevention or treatment of chronic diabetogenous complications.

SUMMARY OF THE INVENTION

With a view toward obtaining a novel aldose reductase inhibitor, the present inventors isolated a number of microorganisms from soil and investigated the aldose reductase inhibitory activities of substances produced by the microorganisms. As a result, it has been found that certain microorganisms of the Pseudeurotium produce a novel aldose reductase inhibitor.

The inhibitor has also been confirmed to be a novel aldose reductase inhibitor from various physiochemical and biological properties thereof and has now been named "aldostatin".

Figure 1:
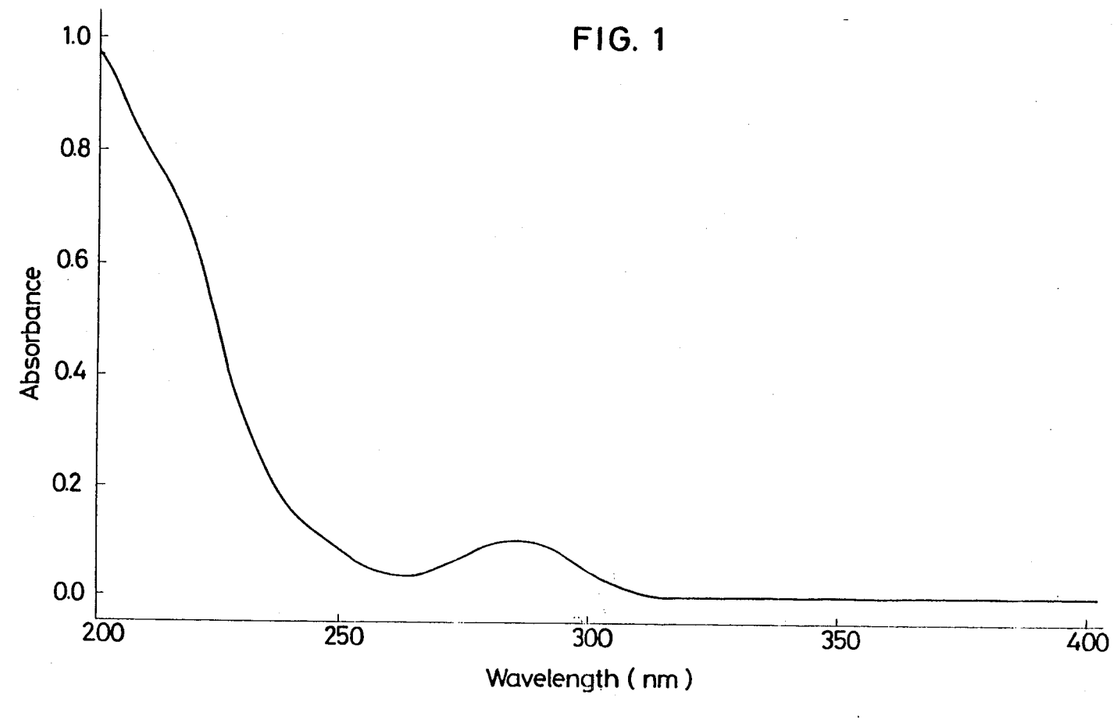
FIG. 1 shows a UV absorption spectrum of the physiologically-active substance of this invention, "aldostatin", in a neutral solution.
Figure 2:
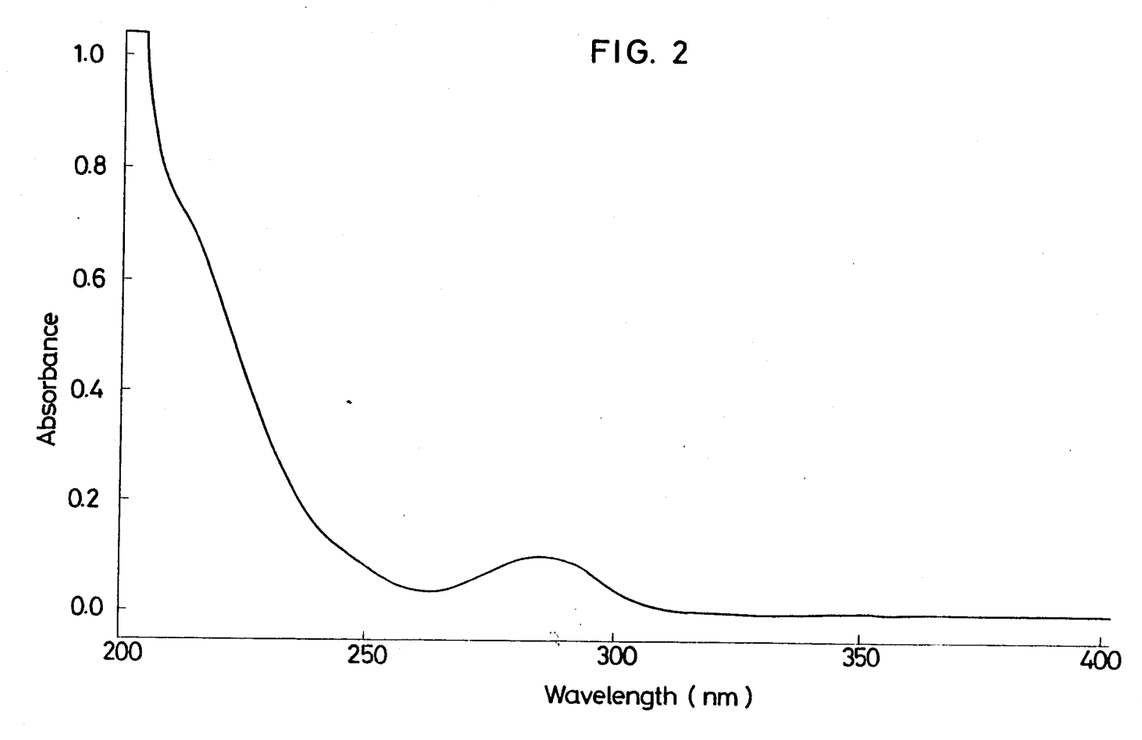
FIG. 2 shows a UV absorption spectrum of aldostatin in an acidic solution.
Figure 3:
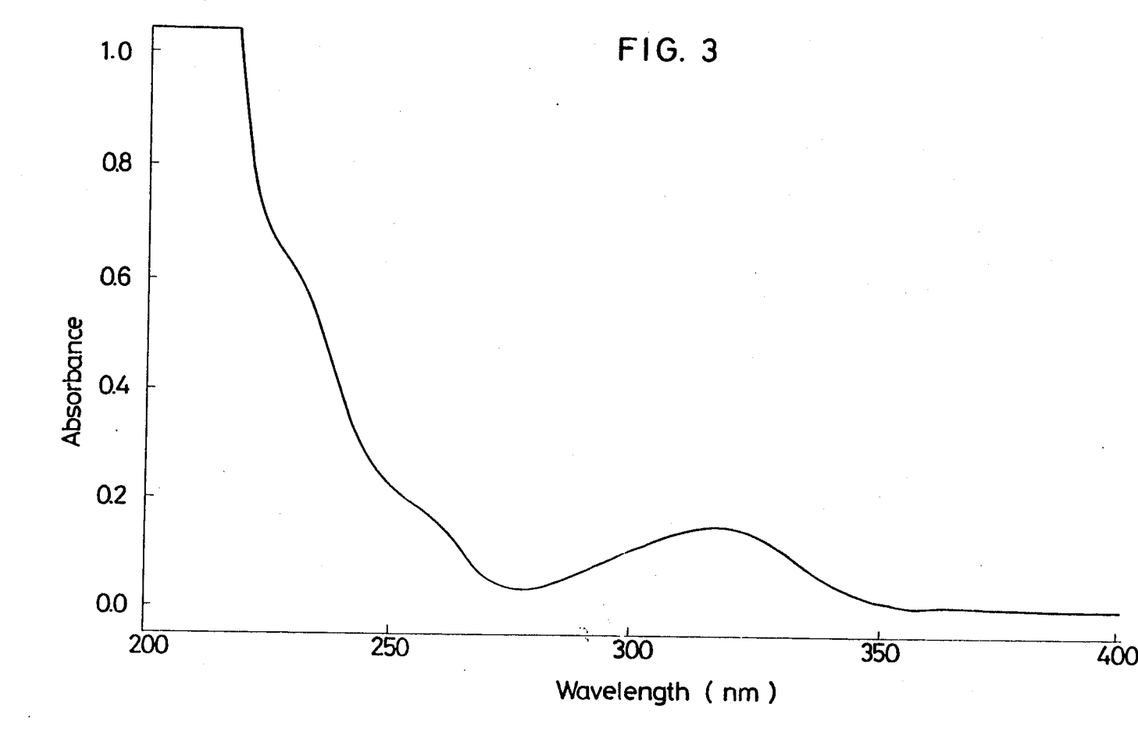
FIG. 3 shows a UV absorption spectrum of aldostatin in an alkaline solution.
Figure 4:
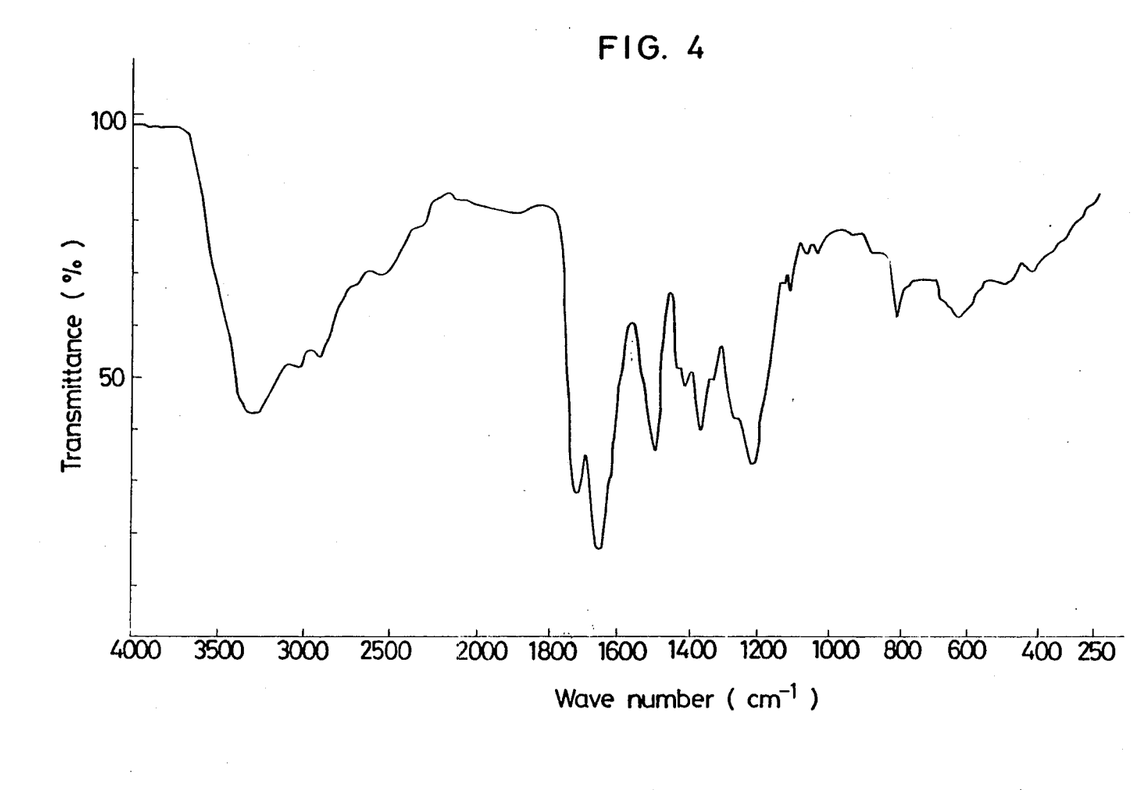
FIG. 4 shows an IR absorption spectrum of aldostatin.
Figure 5:
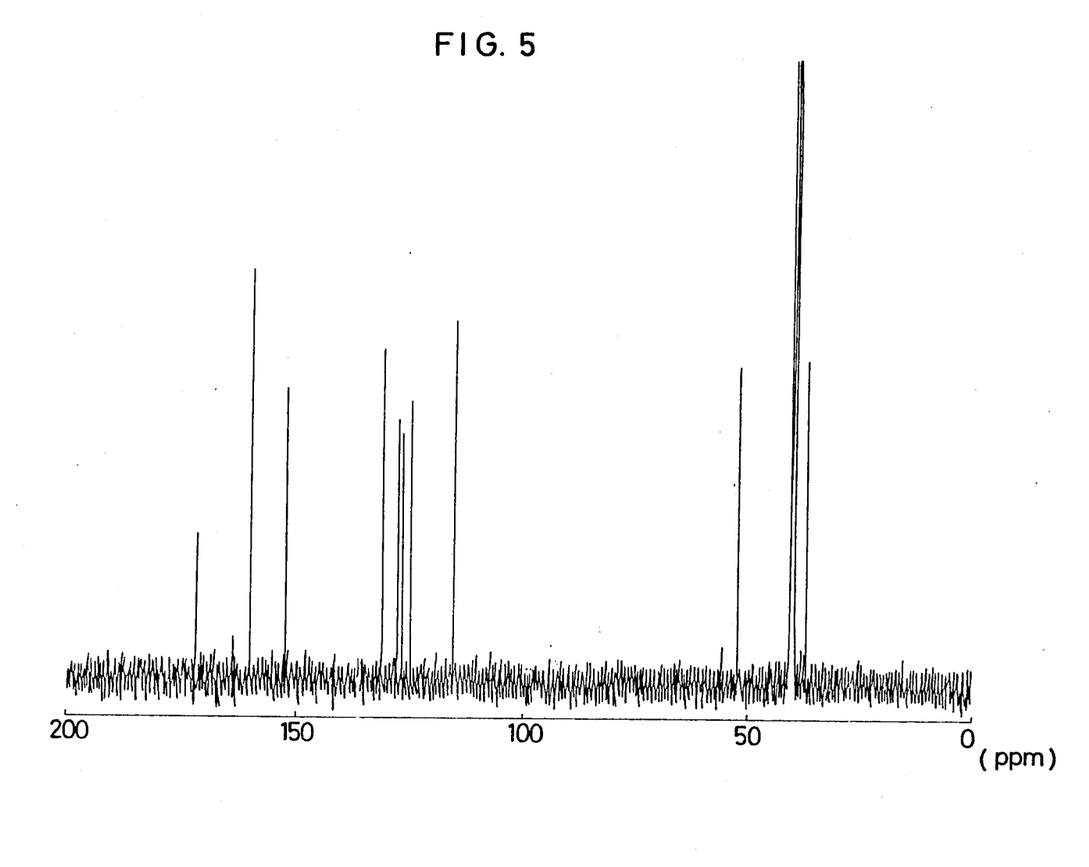
FIG. 5 shows a $^{13}$C-NMR spectrum of aldostatin.

Accordingly, an object of this invention is to provide a physiologically-active substance "aldostatin" having the following properties:

(a) distinction of acidic, neutral or basic:
    acidic substance
(b) elemental analysis:
    C = 57.20 ± 2.0
    H = 4.70 ± 1.0
    N = 6.97 ± 1.5
(c) measured molecular weight:
    $(M + H)^+$ 417 (by the $FAB_{mass}$ method)
(d) estimated molecular formula:
    $C_{20}H_{20}N_2O_8$
(e) UV absorption spectrum:
    (1) aqueous neutral solution
    $\lambda_{max}$ 285 ± 2 nm ($E^{1\%}_{1cm}$ 135 ± 20)
    (FIG. 1)
    (2) aqueous acidic solution:
    $\lambda_{max}$ 285 ± 2 nm ($E^{1\%}_{1cm}$ 135 ± 20)
    (FIG. 2)
    (3) aqueous alkaline solution:
    $\lambda_{max}$ 230 ± 4 nm sh, 257 ± 4 nm sh,
    316 ± 2 nm ($E^{1\%}_{1cm}$ 195 ± 20)
    (FIG. 3)
(f) IR absorption spectrum (KBr; $cm^{-1}$):
    3300, 3030, 2920, 1720, 1650, 1495, 1410,
    1370, 1335, 1220. (FIG. 4)
(g) $^{13}$C—NMR spectrum ($d_6$-DMSO, 100 MHz, internal standard DMSO = 39.5 ppm; δ ppm):
    171.7(s), 160.1(d), 152.1(s), 131.7(d),
    128.2(d), 127.1(s), 125.1(s), 125.1(s), 115.3(d),
    52.1(d), 35.9(t). (FIG. 5).
(h) solubility:
    soluble: water, methanol, and dimethylsulfoxide.
    slightly soluble: acetone, ethyl acetate, and chloroform.
    insoluble: benzene, hexane and petroleum ether
(i) color reaction:
    positive: $KMnO_4$ and $FeCl_3$.
    negative: ninhydrin, Molisch and Fehling.

Another object of this invention is to provide a method for the production of a physiologically-active novel substance "aldostatin", which comprises culturing an "aldostatin"-producing microorganism of the Pseudeurotium in a culture medium and then collecting "aldostatin" from the culture broth.

Aldostatin of this invention inhibits the aldose reductase activity and as a consequence, avoids abnormal accumulation of sorbitol, galactitol, etc. It is therefore effective for the treatment of chronic complications such as cataract, retinopathy and neuropathy caused by diabetes renalis.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE INVENTION AND PREFERRED EMBODIMENT

As a practical example of the microorganism useful for the production of the physiologically-active substance "aldostatin" of this invention, may be mentioned the M4109 strain of the Pseudeurotium which the present inventors isolated from the soil of a farm land in Kannami, Tagata-gun, Shizuoka, Japan. Its mycological characteristics are as follows:

(A) Growth in Various Culture Media

(1) Czapek's Agar

At 26° C., the growth is rather slow. It grows to a diameter of 16–17 mm in 7 days of culture and to 28–29 mm in 14 days of culture. The lawn is thin, flat and velvet-like. Only white hyphae grow. No ascocarp is formed. Peripheries are smooth. Neither exudate nor diffusible pigment occurs. The reverse is white - yellowish white (1A2). No growth at 37° C.

(2) Malt Ex. Agar:

At 26° C., the growth is rather slow. It grows to a diameter of 21–22 mm in 7 days of culture and to 30–31 mm in 14 days of culture. The lawn is thin and flat but is slightly swollen at a central part. White hyphae grow at the beginning but as the culture proceeds, a number of ascocarps are formed underneath white aerial mycelia so that the color changes to light grey (1C1)-medium grey (1E1). Peripheries are smooth. Neither exudate nor diffusible pigment occurs. The reverse is yellowish white (4A1)-pale yellow (4A2) at an area bearing hyphae and olive grey (1E2) at another area with ascocarps formed therein. No growth at 37° C.

(3) Potato Dextrose Agar

At 26° C., the growth is rather slow. It grows to a diameter of 19–20 mm in 7 days of culture and to 30–31 mm in 14 days of culture. The lawn is thin and flat but is slightly swollen at a central part. White hyphae grow at the beginning but as the culture proceeds, a number of ascocarps are formed underneath white aerial mycelia so that the color changes to medium grey (1E1). Peripheries are smooth. A colorless exudate is slightly released but no diffusible pigment occurs. The reverse is olive grey (1F2). No growth at 37° C. Color names and signs follow the method described by A. Kormerup and J. H. Wanscher in "Methuen Handbook of Color" 3rd ed., Eyre Methuen, London, 1978.

(B) Various Physiological Properties

Growable pH: 3.2–9.6
Optimum pH for growth: 3.6–6.4
Growable temperature: 19°–30° C.
Optimum temperature for growth: 22°–26° C.

(C) Microscopic Morphological Characteristics

Formation of closed ascocarps. The closed ascocarps are blackish brown, spherical, 80–180 μm in diameter, and in the form of naked asci. The ascocarp walls are of somewhat skin-like nature, are dark brown. They are composed of a single layer and do not contain any special stitch mechanism. Constituent cells of the ascocarp walls have irregular polygonal shapes, the diameters of which range from 5 μm to 15 μm. Asci are scattered at random in closed ascocarps, have egg-like, pear-like or oval shapes, contain 8 spores, and are 8–11×7–9 μm. Ascospores are spherical and are each formed of a single cell. Their walls are thick and are dark brown. Diameters: 3–4 μm. Neither germ pores nor slits are contained. They look like Sporothrix in the conidial stage. Conidia are formed in the form of the sympodiosporae type at small tooth-like tips of conidium-forming cells. The conidia are colorless, are each formed of a single cell, are 5–7.5×2.5–3.5 μm, have either oval shapes or inverted egg-like shapes, and are slightly thinner at basal portions thereof. Walls are smooth. Conidium-forming cells occur vertically from aerial hyphae, are 8–40×3–5 μm, are not branched, are slightly swollen at central parts, and are tapered toward their free ends. The conidiumforming portions lengthen new growing points one after another.

The mycological characteristics of the above microorganism have been described above. Since it grows through the ascigenous stage (complete stage), the above microorganism is considered to belong to the genus of Ascomycetes. Owing to such characteristic properties that closed ascocarps are formed, ascocarps are irregularly scattered therein, and ascospores are formed of single cells and contain no germ pores or slits, the above microorganism is classified under the ordo of Eurotiales. There are about 50 genera under the ordo of Eurotiales. The above microorganism has however been judged to fall under the genus of Pseudeurotium for such characteristic properties that its closed ascocarps are dark brown, are formed of polygonal cells and have no stitch mechanism, and ascospores are small, brown and smooth, and conidial stages are Sporothrix like. Three species have been recognized by now under the genus of Pseudeurotium, namely, *Pseudeurotium ovalis*, *Pseudeurotium punctatum* and *Pseudeurotium zonatum*. Although ascospores of *Pseudeurotium ovalis* and *Pseudeurotium punctatum* have oval - egg-like shapes, the present microorganism M4109 contains spherical ascospores characteristic to *Pseudeurotium zonatum*. As a result of detailed observation, the present strain M4109 was identified as a *Pseudeurotium zonatum* and was hence named "*Pseudeurotium zonatum* M4109". This microorganism has been deposited under FRI Deposition FERM P-8614, Fermentation Research Institute, Agency of Industrial Science and Technology, Ministry of International Trade and Industry, the Japanese Government.

Upon culture of such a microorganism of the Pseudeurotium which produces the physiologically-active substance "aldostatin", a material which the microorganism can metabolize, such as glucose, starch, sucrose, dextrin, molasses, glycerol, oil or fat, an organic acid or the like may be used as a carbon source for a culture medium. As a nitrogen source, an organic or inorganic nitrogen-containing compound such as soybean meal, cotton seed flour, CSL, meat extract, peptone, yeast extract, germ, urea, ammonium sulfate, ammonium nitrate, ammonium phosphate, ammonium chloride or the like may be employed. Besides, inorganic salts such as NaCl, KCl, $CaCO_3$, $MgSO_4$, $KH_2PO_4$, $Na_2HPO_4$, $FeSO_4$, $MnCl_2$, $CoCl_2$, $ZnSO_4$ and $CaSO_4$ may also be used suitably either singly or in combination. Vitamins such as vitamin $B_1$ and biotin, a deforming agent such as silicone oil and/or a surfactant such as a polyalkylene glycol ether may also be added to culture media as needed. In addition, it is also feasible to add one or more organic and/or inorganic substances which promote the growth of the microorganism and stimulate the production of aldostatin.

For the culture of the above microorganism, any one of conventional culture methods for microorganisms may be employed. Although both solid culture and liquid culture are usable, aerated stirring culture is preferred. A suitable culture temperature can be chosen within a temperature range in which the microorganism is allowed to grow and to produce aldostatin. The culture temperature may however be 19°–30° C., espe- cially, 22°-26° C. The culture may be terminated by judging the time at which aldostatin has reached its maximum potency. Although the actual number of days required for the culture varies to a certain extent depending on conditions, 2-7 days, especially, 3-5 days are preferred.

In order to collect the physiologically-active substance "aldostatin" from a culture broth obtained in the above-described manner, it is possible to follow suitably any one of separation methods which are routinely used upon collection of intermediates, produced by general microorganisms, from their culture broths. For example, cells are removed from a culture broth by either filtration or centrifugation since aldostatin shows properties of water-soluble acidic substances and is primarily contained in the filtrate of the culture broth. The thus-obtained filtrate of the culture broth is adsorbed on a suitable carrier, followed by selective desorption of the effective substance with a suitable solvent. As a carrier of a chromatography employed for the desorption, a material making use of differences in adsorptiveness such as activated carbon, silica gel, alumina, cellulose powder or a synthetic adsorptive resin, a material utilizing differences in functional groups such as an anion exchange resin or anion exchange cellulose, or a material relying upon differences in molecular weight such as a molecular sieve carrier can be advantageously used. In order to elute the target compound "aldostatin" from such a carrier, water-containing organic solvents, namely, water-containing acetone, water-containing methanol and water-containing acetonitrile, acids, alkalis and buffers, aqueous solutions containing inorganic or organic salts, etc. may be used in a suitable combination, although their combination varies depending on the kind and properties of the carrier.

The inhibitor of this invention obtained in a crude form by the above-mentioned chromatography can be subjected further to a preparative high-performance liquid chromatography so as to purify same. In detail, the pH of the filtrate is adjusted to about 4. It is then caused to pass through a column packed with a synthetic adsorptive resin as a carrier, for example, "DIAION HP-20" (trade name; product of Mitsubishi Chemical Industries, Ltd.), "Amberlite XAD-II" (trade name; product of Rohm and Haas Company) or the like, whereby the inhibitor of this invention contained in the filtrate is adsorbed. The thus-adsorbed inhibitor of this invention is then eluted with a water-containing alcohol or water-containing acetone. Fractions containing the thus-eluted inhibitor are concentrated and are then adsorbed on alumina or silica gel. It can thereafter be eluted with a solution of aqueous ammonia in acetonitrile or with a water-containing alcohol solution. The thus-fractionated eluate fractions are processed into powder through steps such as concentration and lyophilization.

If the purity of the thus-obtained powder is low, high-performance liquid chromatography can be advantageously used for further purification. As useful carrier, may be mentioned "Lichroprep RP-18 Gel" (trade name; product of MERCK & CO. INC.) or "YMC Gel ODS 30/60" (trade name; product of Yamamura Chemical Laboratories, Inc.) by way of example. As a mobile phase, it is possible to use a mixture of methanol or acetonitrile and an aqueous solution of a salt or the like. Aldostatin obtained in the above manner usually contains one or more salts employed for its purification. For desalting same, it is advantageous to use chromatography which employs a synthetic adsorbent. Namely, an aqueous aldostatin solution containing the salts is adjusted to about pH 4.0 with dilute hydrochloric acid, followed by its chromatography on "DIAION HP-20". After washing the carrier with water, active fractions are eluted with a water-containing alcohol. Upon concentration and lyophilization of the eluate, aldostatin is obtained in its free form.

The thus-obtained aldostatin of this invention has the following physical and chemical properties. From these properties, it is considered to be a compound represented by the following estimated structural formula:

[N—formyl-L-bityrosine]

Figure 6:
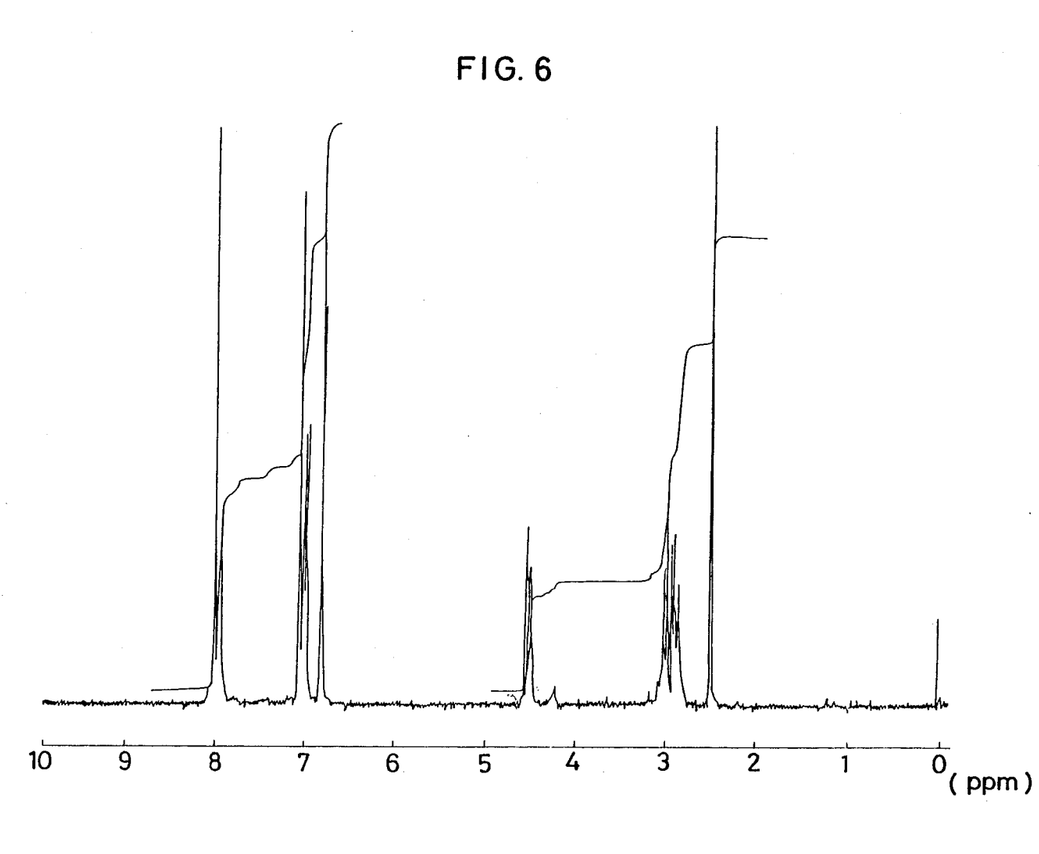
FIG. 6 shows a $^1$H-NMR spectrum of aldostatin.

Physiochemical properties (1) external appearance: white powder.
(2) distinction of acidic, neutral or basic: acidic substance
(3) melting point: 144-146° C.
(4) elemental analysis:
C = 57.20 ± 2.0
H = 4.70 ± 1.0
N = 6.97 ± 1.5
(5) measured molecular weight:
$(M + H)^+$ 417 (by the $FAB_{mass}$ method)
(6) estimated molecular formula: $C_{20}H_{20}N_2O_8$
(7) specific rotation $[\alpha]_D^{26}$
$+ 59.0° ± 10° (C = 0.50, H_2O)$
(8) UV absorption spectrum:
(1) aqueous neutral solution:
$\lambda_{max}$ 285 ± 2 nm ($E_{1\ cm}^{1\%}$ 135 ± 20) (FIG. 1)
(2) aqueous acidic solution:
$\lambda_{max}$ 285 ± 2 nm ($E_{1\ cm}^{1\%}$ 135 ± 20) (FIG. 2)
(3) aqueous alkaline solution:
$\lambda_{max}$ 230 ± 4 nm sh, 257 ± 4 nm sh, 316 ± 2 nm ($E_{1\ cm}^{1\%}$ 195 ± 20) (FIG. 3)
(9) IR absorption spectrum (KBr; $cm^{-1}$):
3300, 3030, 2920, 1720, 1650, 1495, 1410, 1370, 1335, 1220. (FIG. 4)
(10) $^{13}C$—NMR spectrum (d$_6$-DMSO, 100 MHz, internal standard DMSO = 39.5 ppm; δ ppm):
171.7(s), 160.1(d), 152.1(s), 131.7(d), 128.2(d), 127.1(s), 125.1(s), 115.3(d), 52.1(d), 35.9(t). (FIG. 5).
(11) $^1H$—NMR spectrum (d$_6$-DMSO, 400 MHz, internal standard TMS; δ ppm):
8.02(1H,S), 7.98(1H,d), 7.05(1H,s), 6.97(1H,d), 6.80(1H,d), 4.50(1H,q), 2.96(2H,m). (FIG. 6)
(12) thin layer chromatography (TLC): spot film, "Silica Gel f" (trade name; product of Tokyo Kasei Kogyo Co., Ltd.)

| Solvent system | Rf value |
|---|---|
| BuOH:AcOH:H$_2$O (4:1:1) | 0.63 |
| CHCl$_3$:MeOH:H$_2$O (5:5:1) | 0.31 |
| EtOAc:MeOH:H$_2$O (5:5:1) | 0.27 |
| CHCl$_3$:MeOH:AcOH:H$_2$O (10:5:1:1) | 0.36 |
| PrOH:H$_2$O (4:1) | 0.25 |

(13) high-performance liquid chromatography (HPLC):
carrier: "Hitachi Gel #3056" (trade name; product of Hitachi Ltd.)
mobile phase: 8% methanol with 1% ammonium acetate, 0.8 ml/min, Rt = 4.2 (min).

-continued

[N—formyl-L-bityrosine]

Physiochemical properties (14) solubility:
- soluble: water, methanol, and dimethylsulfoxide.
- slightly soluble: acetone, ethyl acetate, and chloroform.
- insoluble: benzene, hexane and petroleum ether (15) color reaction:
- positive: $KMnO_4$ and $FeCl_3$.
- negative: ninhydrin, Molisch and Fehling.

Biological Properties (1) Aldose Reductase Inhibitory Activity

The preparation of an aldose reductase and the quantitative analysis of its enzymatic activity were effected in accordance with the method described by Hayman et al. in "Journal of Biological Chemistry" 240, 877 (1965). It was a partially purified aldose reductase derived from bovine lenses that was employed as an enzyme. Placed in a quartz cell in a spectrophotometer photometer was 2.4 ml of a $5 \times 10^{-5}M$ NADPH solution dissolved in 2/15M phosphate buffer (pH 6.0), 0.4 ml of 15 milliunits/ml solution of the enzyme and 0.1 ml of an aqueous aldostatin of one of various concentration. The contents were pre-incubated at 37° C. for 4 minutes. The reaction started by adding 0.1 ml of 0.015M D,L-glyceraldehyde into the quartz cell. The reduction of the absorbance at 340 nm was traced at 37° C. for 4 minutes. At that time, the value (B) of tan $\theta$ was determined. Similarly, the reduction of the absorbance at 340 nm without addition of the inhibitor "aldostatin" was tracked. At that time, the value (A) of tan $\theta$ was determined. Percent inhibition (%) was calculated as follows.

$$\text{Percent inhibition (\%)} = \frac{A - B}{A} \times 100$$

The amount of inhibitor for 50% inhibition was expressed as $IC_{50}$.

The aldose reductase inhibitory activity of aldostatin determined in the above-described manner is as follows:

| Substrate (substrate concentration) | $IC_{50}$ (μg/ml) |
| --- | --- |
| glyceraldehyde ($5.0 \times 10^{-4}$ M) | 0.5 |
| glucose ($5.0 \times 10^{-2}$ M) | 1.1 |

(2) Acute Toxicity

Aldostatin showed no toxic effect when it was administered i.v. into mice at a dose of 200 mg/kg.

Aldostatin of this invention may also be converted into its metal salts and ammonium salt a needed. Exemplary metal salts include its sodium salt, potassium salt, lithium salt, calcium salt, etc.

A drug containing aldostatin of this invention may be formulated into dosable preparations such as injections, nasal drops, suppositories and the like in addition to its orally administrable preparations and eye drops. The drug may be prepared by a method known per se in the art while incorporating aldostatin or a salt thereof suitably in an amount of 100 μg–500 mg per administration.

EXAMPLE

This invention will next be described by the following Example. It should however be borne in mind that the present invention is not limited by the following Example.

EXAMPLE 1

(i) The strain of *Pseudeurotium zonatum* M4109 (FRI Deposition FERM P-8614), which had been allowed to grow by slant culture on nutrient agar, was inoculated in a 500 ml Erlenmeyer flask containing 100 ml of a sterilized culture medium of 2% glucose, 2% starch, 2% soybean flour, 0.25% NaCl, 0.5% yeast extract and 0.35% $CaCO_3$ (pH 6.5). The contents were subjected to shaking culture at 26° C. for 3 days. The resultant culture broth was used as a seed culture.

(ii) Next, twenty liters of a culture medium containing 2% glucose, 1% peptone, 1% CSL, 0.2% $KH_2PO_4$ and 0.1% $MgSO_4.7H_2O$ (pH 6.5) were poured 100 ml by 100 ml in 500 ml Erlenmeyer flasks. After sterilizing the contents at 120° C. for 20 minutes, each flask was inoculated with 4 ml of the seed culture, followed by shaking culture a 26° C. for 4 days.

(iii) The culture broth (20 l) obtained in the above procedure (ii) was adjusted to pH 4, followed by filtration to obtain 17 l of a culture broth filtrate. A majority of aldostatin was contained in the filtrate. The culture broth filtrate was subjected.to chromatography on "DIAION HP-20" (1.6 l). After the column was washed with 8 l of water, active fractions were eluted with 50% methanol water. The active eluates (4 l) were concentrated to 1 l under reduced pressure. After adjustment with aqueous ammonia to pH 6.5, the resultant solution was charged in a column of 500 ml of "DIAION HP-20". Upon elution with water, a majority of the activity was contained in both the eluate (1 l) and the water-eluted fractions (1.3 l).

(iv) Under reduced pressure, 2.3 l of these active fractions was concentrated to about 20 ml, followed by an addition of 200 ml of methanol. The resulting precipitate was removed by centrifugation so as to obtain a centrifugal supernatant. The supernatant was charged in an alumina column (200 ml) which had in advance been filled with methanol. After washing the column with 1 l of methanol and 1 l of acetonitrile, the column was developed with a 2:1 mixed solvent of acetonitrile and 1N aqueous ammonia. The eluate was fractionated 18 g by 18 g so that the active substance of this invention was eluted in Fraction Nos. 61–190. These fractions were collected and then concentrated under reduced pressure. The residue was charged in a Sephadex G-15 column (1650 ml), followed by development with water. The eluate was fractionated 15 g by 15 g. The active substance was eluted in Fraction Nos. 65–80. These fractions were collected and then concentrated under reduced pressure, followed by lyophilization to obtain 350 mg of white powder.

(v) The white powder obtained in the above procedure (iv) was subjected to preparative high-performance liquid chromatography on a column of "Lichroprep RP-18" (trade name; product of MERCK & CO., INC.) as a carrier, the particle sizes of which ranged from 25 μm to 40 μm. The column was then eluted and fractionated with a 3% aqueous solution of methanol, which contained 0.5 of ammonium acetate. The resultant fractions were each analyzed by liquid chromatography. Fractions showing the single peak characteristic to aldostatin were collected. The thus-collected active fraction was adjusted to pH 4.0 with 0.5N hydrochloric acid. It was thereafter caused to pass through a column packed with 50 ml of "DIAION HP-20". After washing the column with 250 ml of water, the column was eluted with 150 ml of a 50% aqueous solution of methanol. The eluate was concentrated, followed by lyophilization to obtain 75 mg of aldostatin as white powder in its free form.

Having now fully described the invention, it will be apparent to one of ordinary skill in the art that many changes and modifications can be made thereto without departing from the spirit or scope of the invention as set forth herein.

What is claimed is:

1. A physiologically-active substance "aldostatin" having the following properties:

| | | |
|---|---|---|
| (a) | distinction of acidic, neutral or basic: | |
| | acidic substance | |
| (b) | elemental analysis: | |
| | C = 57.20 ± 2.0 | |
| | H = 4.70 ± 1.0 | |
| | N = 6.97 ± 1.5 | |
| (c) | measured molecular weight: | |
| | $(M + H)^+$ 417 (by the $FAB_{mass}$ method) | |
| (d) | estimated molecular formula: | |
| | $C_{20}H_{20}N_2O_8$ | |
| (e) | UV absorption spectrum: | |
| | (1) aqueous neutral solution | |
| | $\lambda_{max}$ 285 ± 2 nm ($E^{1\%}_{1cm}$ 135 ± 20) | |
| | (FIG. 1) | |
| | (2) aqueous acidic solution: | |
| | $\lambda_{max}$ 285 ± 2 nm ($E^{1\%}_{1cm}$ 135 ± 20) | |
| | (FIG. 2) | |
| | (3) aqueous alkaline solution: | |
| | $\lambda_{max}$ 230 ± 4 nm sh, 257 ± 4 nm sh, | |
| | 316 ± 2 nm ($E^{1\%}_{1cm}$ 195 ± 20) | |
| | (FIG. 3) | |
| (f) | IR absorption spectrum (KBr; cm$^{-1}$): | |
| | 3300, 3030, 2920, 1720, 1650, 1495, 1410, | |
| | 1370, 1335, 1220. (FIG. 4) | |
| (g) | $^{13}$C—NMR spectrum (d$_6$-DMSO, 100 MHz, internal standard DMSO = 39.5 ppm; δ ppm): | |
| | 171.7(s), 160.1(d), 152.1(s), 131.7(d), | |
| | 128.2(d), 127.1(s), 125.1(s), 125.1(s), 115.3(d), | |
| | 52.1(d), 35.9(t). (FIG. 5). | |
| (h) | solubility: | |
| | soluble: | water, methanol, and dimethylsulfoxide. |
| | slightly soluble: | acetone, ethyl acetate, and chloroform. |
| | insoluble: | benzene, hexane and petroleum ether |
| (i) | color reaction: | |
| | positive: KMnO$_4$ and FeCl$_3$. | |
| | negative: ninhydrin, Molisch and Fehling. | |

2. A method for the production of a physiologically-active substance aldostatin, as defined in claim 1, which comprises culturing *Pseudeurotium zonatum* M4109 strain in a culture medium until a sufficient amount of aldostatin is produced, and then collecting aldostatin from the culture broth.

* * * * *